United States Patent [19]

Rondum et al.

[11] Patent Number: 5,213,678

[45] Date of Patent: May 25, 1993

[54] METHOD FOR INHIBITING FOULANT FORMATION IN ORGANIC STREAMS USING ERYTHORBIC ACID OR OXIMES

[75] Inventors: Kaj D. Rondum, Budd Lake, N.J.; Guy A. DeVicaris, Quakertown, Pa.; Dwight E. Emerich, Lincoln Park, N.J.

[73] Assignee: Ashchem I.P., Inc., Dublin, Ohio

[21] Appl. No.: 652,943

[22] Filed: Feb. 8, 1991

[51] Int. Cl.⁵ .............................................. C10G 9/16
[52] U.S. Cl. ................................. 208/48 AA; 203/8; 203/9; 585/2; 585/3; 585/4; 585/950
[58] Field of Search ............... 203/8, 9; 208/49 AA; 585/2, 3, 4, 5

[56] References Cited

U.S. PATENT DOCUMENTS

| | | | |
|---|---|---|---|
| 2,407,861 | 9/1946 | Wolk | 203/9 |
| 2,446,969 | 8/1946 | Welch et al. | 208/48 AA |
| 2,483,778 | 8/1946 | Morrell et al. | 585/4 |
| 2,947,795 | 8/1960 | Keown | 585/4 |
| 3,148,225 | 9/1964 | Albert | 260/669 |
| 3,793,187 | 2/1974 | Marx et al. | 208/48 AA |
| 4,237,326 | 12/1980 | Fuga et al. | 208/48 AA |
| 4,269,717 | 5/1981 | Slovinsky | 252/188.28 |
| 4,487,745 | 12/1984 | Weiss | 422/16 |
| 4,927,519 | 5/1990 | Forester | 208/48 |
| 4,941,926 | 7/1990 | Nakajima | 134/22 |
| 4,956,020 | 9/1990 | Nakajima | 134/22.19 |

FOREIGN PATENT DOCUMENTS 215525 9/1981 Fed. Rep. of Germany .......... 585/2

OTHER PUBLICATIONS

Polymerization of styrene in the presence of N, N-disubstituted hydroxylamines by A. Hrivik, CS-812 37 Bratislava, Jan. 1983 Chem. rvesti 37 (4) 503-509 (1983).

*Primary Examiner*—Theodore Morris
*Assistant Examiner*—Walter D. Griffin
*Attorney, Agent, or Firm*—Wood, Herron & Evans

[57] ABSTRACT

A method for inhibiting fouling in an organic process stream by adding certain oximes, hydrazine, erythorbic acid, carbohydrazide, or mixtures thereof. The antifoulant is added to the organic stream as an aqueous solution.

12 Claims, No Drawings

METHOD FOR INHIBITING FOULANT FORMATION IN ORGANIC STREAMS USING ERYTHORBIC ACID OR OXIMES

FIELD OF THE INVENTION

The invention relates to a method for inhibiting formation of foulants in an organic stream by the addition of a composition containing an effective amount of a compound selected from the group consisting of hydrazine, erythorbic acid, carbohydrazide, certain oximes, and mixtures thereof.

BACKGROUND OF THE INVENTION

In a wide variety of applications wherein organic compounds are used or processed, one must be concerned about the occurrence of fouling in the processing equipment. Fouling in an organic stream or system occurs as a result of polymerization or other reaction of at least a portion of the organic components in the stream or system to form a higher molecular weight product having reduced solubility in the organic components. The reduced solubility causes the higher molecular weight product, i.e. the foulant, to separate from the organic components and clog or obstruct transfer lines, settle out from the components, and otherwise coat the surfaces of the processing equipment. The formation of undesirable foulants occurs in process streams having only organic as well as both organic and aqueous phases. The aqueous phase may be merely water entrained in the organic stream during processing, but also includes the water added to quench or cool a reaction or to remove certain water soluble components from the organic stream by a process step, such as steam stripping. Where water is present in the organic stream, the presence of water-soluble dissolved materials which may catalyze or enhance polymerization or other reaction must be considered.

Reaction occurs because the organic compounds are subjected to conditions sufficient to cause modification of the chemical structure of one or more of the organic components of the stream or system. Conditions which affect reactivity include temperature, pressure, pH and presence of trace metals and other contaminants. For example, it is known that in the process of thermally cracking a feedstock blend of naphtha and gas oil to produce short chain thermal cracking products such as ethylene, propylene, ethane, treated pyrolysis gasoline and various mixed hydrocarbon streams, the existing processing temperatures, pressures and presence of trace contaminants cause further reaction of one or more of the thermal cracking products to create oligomers, polymers and oxidized products which are capable of fouling the processing equipment.

The secondary reaction products formed in process streams such as that described above are undesirable for several reasons. First, if the secondary reaction product is soluble in the thermal cracking product stream, it exists as an impurity which must be removed by distillation, solvent extraction, or other separation technique. If alternatively the secondary reaction product is insoluble in the process stream, it tends to settle out of the stream and accumulate in the low-lying portions of the process stream transport system. The insoluble secondary reaction product may also plate out from the stream and coat all exposed walls of the process stream transport system, including piping, pumps, heat exchanger cores, storage tanks, and the like. In either case, the secondary reaction products eventually form substantial deposits within the process stream transport system. These deposits can cause damage to the transport system by building up significant over-pressures within the system, and by limiting the through-put of desirable product. Ultimately, these deposits must be removed, typically by shutting down the entire system and physically removing the deposits. This results in substantial cost, both in lost operating time and in maintenance.

The chemical reactions occurring in organic streams which produce foulants are varied and complex. The most prevalent cause of fouling in an organic stream results from polymerization of one or more organic components of the organic stream. Typically the undesirable foulant polymers are formed by reactions of unsaturated hydrocarbons. Formation of undesirable foulants can be enhanced by the presence of trace organic materials containing hetero atoms such as nitrogen, oxygen, and sulfur.

Polymers are formed in organic streams by free radical chain reactions, which consist of an initiation phase followed by a propagation phase. A free radical is formed from a molecule by the removal of a single electron, the free radical thus having a single odd electron remaining which is available for further reaction. This free radical then reacts with other molecules or free radicals in the organic stream to either propagate the chain or to terminate the chain. The presence of oxygen in the organic stream can itself accelerate the polymerization process by facilitating formation of free radicals. Also, trace amounts of metal impurity carried along from earlier catalytic processes or from the walls of the metal piping itself can act as generators of free radicals. A more detailed explanation of the various reactions involved in the formation of foulants is found in U.S. Pat. No. 4,927,519, issued May 22, 1990, which is incorporated herein by reference.

It is desirable, and highly recommended, to minimize the presence of those materials which cause or enhance formation of foulants, such as oxygen, metals, free radicals and the like. Additional mechanical purification of the organic stream, such as by filtration or centrifugation, aids in reducing the presence of trace metal particles and other insoluble contaminants. Where possible, vacuum and heat are known to be applied to such streams to deaerate or deoxygenate the process stream containing organic materials both with and without water. However, these mechanical treatment methods still leave low levels of contaminants in the stream which subsequently react.

It is known to employ chemical treatments to control fouling deposit formation. U.S. Pat. No. 4,927,519 discloses an anti-foulant composition added directly to a hydrocarbonaceous stream comprising a basic anti-fouling compound wherein one component is selected from the group consisting of alkyl phosphonate phenate sulfide, alkaline earth alkyl phosphonate phenate sulfide, and amine neutralized alkyl phosphonate phenate sulfide, and mixtures thereof, combined with at least one additional compound which is an effective anti-oxidant, a corrosion-inhibiting compound, or a metal deactivator. U.S. Pat. No. 3,148,225 discloses the use of certain lower alkyl N, N-dialkylhydroxylamines to inhibit popcorn polymer formation during the preparation of synthetic rubber from styrene and butadiene. Notwithstanding the above materials for use in limiting formation of foulants as well as additional known additives having anti-foulant properties, there remains a continued need for alternate and improved methods for inhibiting foulant formation.

SUMMARY OF THE INVENTION

It has been found unexpectedly that the fouling tendencies of organic compounds in contact with water are inhibited in the process stream by adding an effective amount to the water of one or more compounds selected from the group consisting of lower alkyl or aryl oximes, hydrazine, erythorbic acid, carbohydrazide and mixtures thereof. Erythorbic acid is a diastereoisomer of ascorbic acid, and is also known as isoascorbic acid. In like manner, ascorbic acid will also function as an antifoulant. Hereinafter, in the specification and claims, the term "erythorbic acid" is also meant to include ascorbic acid.

In the case of the oxime compounds, it has been found that one or more materials derived from the oxime are active agents in inhibiting fouling of the organic compounds. The active agents derived from the oxime are formed most readily in the presence of water at elevated temperatures, preferably at an alkaline pH. It is believed that the agent or agents formed by treating the particular oxime compound scavenges free radicals in the stream containing the organic materials which includes those capable of further polymerizing or otherwise reacting.

In addition to effectively inhibiting the polymerization or other free radical-based reaction of one or more components of the organic material stream, the antifoulants used in carrying out the method of this invention have the further advantages of promoting a reducing environment, thereby minimizing the formation of corrosion products. The active agents derived from oximes, as well as hydrazine, erythorbic acid and carbohydrazide, act as oxygen scavengers, to inhibit oxygen corrosion and oxygen induced polymerization. The antifoulants also aid in metal coordination by reducing metallic ions to a lower, more soluble oxidation state. In this state, the metal ions are more easily sequestered or chelated by a separate additive to form a heat stable complex which renders the metal ions unavailable as a catalyst. As reducing agents, hydrazine, erythorbic acid, carbohydrazide and the active agents derived from oximes will passivate metal surfaces, rendering them more corrosion resistant.

DETAILED DESCRIPTION OF THE INVENTION

The invention in its broader aspects relates to a method for inhibiting fouling caused by reaction of organic compounds in contact with water comprising adding to the water an effective amount of a compound selected from the group consisting of hydrazine; erythorbic acid; carbohydrazide; an oxime of the formula:

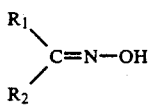

in which $R_1$ and $R_2$ are the same or different and are selected from hydrogen, lower alkyl groups of 1-8 carbon atoms and aryl groups; and mixtures thereof.

It has been determined experimentally that it is not the oximes per se which perform the desired anti-fouling function of this invention. Rather, one or more components formed from the oxime has been found to function to scavenge free radicals and inhibit the polymerization or other reaction of the organic material in contact with the effective component formed from the oxime. The effective component is known to form from oxime in the presence of water. The rate of formation of the effective component increases with increasing temperature. The component does form at room temperature, but the rate of formation is very low. The preferred pH range for formation of the component from oxime is 7 to 9, most preferably 8 to 9. The pH can be below 7 or above 9, and fast scavenger will still form. However, in an acidic environment exposed metal parts are more likely to corrode, causing not only damage to the equipment but also increasing the amount of metal in the process stream available to act as a catalyst. An environment at a pH greater than 9 increases the risk of emulsion formation between the hydrocarbon and water.

The formation of the active component derived from the oxime, labeled "fast scavenger", is a function of both the temperature and the concentration of the oxime. Fast scavenger forms at room temperature in a mixture of oxime and water, but the rate of formation is so slow as to be impractical. Fast scavenger has not been found to form in pure oxime at room temperature. Thus, the method of this invention is believed to require the presence of at least some water during generation of the fast scavenger component.

Fast scavenger may be formed in situ in the organic compounds - water mixture to be protected or it may be formed out of the presence of the mixture and then introduced into the organic compounds - water mixture.

The composition of fast scavenger is not known. It is a relatively unstable species, derived from an oxime, and decomposes under the action of heat, requiring replenishment by breakdown of additional oxime. It is theorized that the fast scavenger component is a free radical thermolysis decomposition product of the oxime. In general, the rate of generation of fast scavenger from oxime will exceed the destruction of fast scavenger by heat. Therefore, a significant and useful concentration of fast scavenger can be maintained.

The amount of fast scavenger needed to prevent fouling of the organic material varies with the type of organic material and the processing conditions to which the organic material is being subjected. Thus, a relatively stable blend of organic compounds, such as saturated hydrocarbons, being processed at a temperature of less than about 100° C. in the absence of oxygen and metal contaminants would not be likely to form appreciable amounts of free radicals which would lead to polymerization. In this instance, very little fast scavenger would be required to scavenge the free radicals formed. Where the organic material has one or more components which are more easily polymerized, especially under conditions of high temperature, pressure, and in the presence of oxygen or trace amounts of metal, the need for scavenging of free radicals is substantially increased. In these instances, higher levels of fast scavenger may be required.

The amount of fast scavenger required can be readily determined by someone skilled in the art, though the determination is primarily qualitative. At insufficient levels of antifoulant, the process stream comprised of organic components, water, antifoulant and other additives will be discolored because of metals contamination and may have an increased viscosity due to polymerization. The antifoulant level can then be adjusted upward to that level where the appearance of the process stream is acceptable. Overdosing is not recommended, as this can form undesirably high levels of ketones or aldehydes corresponding to the starting oxime, which can then destroy fast scavenger. The phenomenon of overdosing is also encountered when using hydrazine and carbohydrazide. Too much of either of these two materials in the process stream tends to form ammonia, which increases the pH of the process stream and increases the potential for emulsion formation.

Typically, oxime is added to the water at a level of 0.1-100 ppm, more preferably 0.5-10 ppm.

Additional compounds which have antifoulant properties are erythorbic acid, hydrazine, and carbohydrazide. The amount of these compounds to be added to the process stream to minimize fouling is determined in substantially the same way as for the oxime. The typical levels of the above compounds to be added to water are similar to those disclosed above for oxime.

In the case of erythorbic acid, where the pH of the environment is basic the acid will convert to a salt having as a cation the positively charged species which is a component of alkaline material used to raise pH. Typically, sodium hydroxide is used to raise pH, but other alkaline materials such as potassium hydroxide, ammonium hydroxide, and the like, may be used.

OPERATING EXAMPLES

The following detailed operating examples illustrate the practice of the invention in its most preferred form, thereby permitting a person of ordinary skill in the art to practice the invention. The principles of this invention, its operating parameters and other obvious modifications thereof will be understood in view of the following detailed procedure.

EXAMPLES 1-13

To demonstrate that fast scavenger inhibits foulant formation instead of oxime itself, an aqueous solution of the oxime was combined with the organic material both with and without treatment at elevated temperature and pressure, with adjusted pH. To form the fast scavenger, methyl ethyl ketoxime ($H_3C(C=NOH)CH_2CH_3$) was added to 800.0 g. of deionized water at a level of 0.1% by weight at pH 9 adjusted with sodium hydroxide This mixture was heated in a one liter stainless steel autoclave at 165.6° C. for one hour, creating a maximum pressure in the autoclave of 100 psig. The mixture was maintained under an inert atmosphere to minimize contact with oxygen. Nitrogen and argon were used interchangeably to maintain the inert atmosphere. The solution was cooled to room temperature and added to a two liter glass reaction flask. The cooled mixture was sparged using an inert gas of either nitrogen or argon used interchangeably to remove residual oxygen from the system.

The organic compound studied in the following runs was n-vinylpyrrolidone ($C_6H_9NO$). This compound was mixed with deionized water containing one of various antifoulant compounds. In the case of the oxime antifoulant pretreated at elevated temperature and pressure with adjusted pH, the treated solution was allowed to cool to room temperature under an inert atmosphere before mixing with the organic compound.

All tests were conducted by charging 800 milliliters of the mixture of deionized water and antifoulant compound into a 2 liter glass reaction vessel. All work was done under a nitrogen or argon atmosphere to minimize presence of oxygen. The n-vinylpyrrolidone monomer was added to the glass vessel, and the contents were heated to 55° C., with vigorous agitation, and held at that temperature for 20 minutes. Then, 2 milliliters of a 2% aqueous solution of V-50 (2,2'-Azobis (2-amidinopropane)) dihydrochloride manufactured by Wako Chemicals U.S.A., Inc. (CAS No. 2997-92-4) was added as a polymerization initiator and the solution was heated to 78° C., with vigorous agitation, and held at that temperature for 4 hours under an inert gas of either nitrogen or argon. The mixture was cooled and checked to determine the presence of polymerized product by measuring the viscosity of the system. Viscosity was measured by a Brookfield Viscometer. A No. 1 spindle was used for low viscosity measurements, and a No. 3 spindle was used for the higher viscosity measurements. Spindle speed in both instances was 60 RPM.

The following table summarizes the results:

TABLE I

| Example | Monomer Dosage | Test Water | Result |
|---|---|---|---|
| 1 | 0.00 | water only | viscosity - 4 centipoise |
| 2 | 158.26 g | water pH 9; no inhibitor | Thick polymer formed, - viscosity 1900 centipoise |
| 3 | 158.26 g | water pH 9; 0.1% methyl ethyl ketoxime not autoclaved* | Thick polymer formed, - viscosity 1800 centipoise |
| 4 | 158.26 g | water pH 9; 0.1% methyl ethyl ketoxime autoclaved* | No polymer formed, - viscosity 4 centipoise |
| 5 | 158.26 g | water pH 9; 0.05% methyl ethyl ketoxime autoclaved* | No polymer formed, viscosity 4 centipoise |
| 6 | 158.26 g | water pH 9; 0.0125% methyl ethyl ketoxime autoclaved* | Polymer formed viscosity 15 centipoise |
| 7 | 158.26 g | water pH 9; 0.00625% methyl ethyl ketoxime autoclaved* | Polymer formed viscosity 1900 centipoise |
| 8 | 158.26 g | water pH 9; 0.1% carbohydrazide | No polymer formed, viscosity 4 centipoise |
| 9 | 158.26 g | water pH 9; 0.1% sodium erythorbate | No polymer formed, viscosity 4 centipoise |
| 10 | 158.26 g | water pH 9; 0.1% sodium sulfite | Polymer formed, viscosity 200 centipoise |
| 11 | 158.26 g | water pH 9; 0.1% hydrazine | No polymer formed, viscosity 4 centipoise |

*"Autoclaving" describes a treatment of an aqueous solution of oxime to form fast scavenger consisting of heating the oxime and water at the adjusted pH in a stainless steel 1 liter autoclave for 1 hour at 165.6° C. Antifoulant concentration is expressed as a weight percentage based on the weight of the deionized water.

As the data demonstrates, an aqueous solution of methyl ethyl ketoxime added to the monomer without autoclaving failed to inhibit fouling. Further, the treated oxime performed satisfactorily in inhibiting fouling at decreasing use levels until reaching the weight concentration of 0.00625% based on weight of the water. Carbohydrazide, sodium erythorbate and hydrazine all performed satisfactorily at the 0.1% concentration.

To be useful in carrying out the method of this invention, the oxime anti-foulant compound is mixed in water to form the fast scavenger species. Thus, it is expected that those oximes having substituents with the molecular weight and structure to render the oxime water soluble under the process conditions will also function satisfactorily.

The compounds used according to the method of this invention are incorporated into the organic stream as an aqueous solution. The antifoulant compounds described herein are introduced to establish a threshold dosage level which results in minimum fouling, determined typically by observation. Thereafter, a dose rate is established to maintain a concentration of the antifoulant in the organic stream sufficient to keep fouling to a minimum. The threshold dosage level and dose rate varies according to the chemical composition of the organic stream; the temperature, pressure and pH of the environment within the processing equipment; the type and metallurgical properties of the processing equipment; the presence of oxygen, other contaminants and trace metals in the organic stream; and the efficiency of the particular antifoulant in the particular organic stream.

For example, in a thermal cracking process stream consisting of gas oil in water operating at 85° C. in mild steel processing equipment, methyl ethyl ketoxime was added as an aqueous solution to reach and maintain a concentration of approximately 1.6 ppm by weight per water content, to minimize fouling.

While the invention has been described in conjunction with specific embodiments thereof, it is evident that many alternatives, modifications, and variations will be apparent to those skilled in the art in light of the foregoing description.

What is claimed is:

1. A method for inhibiting fouling caused by reaction of organic compounds with at least one multiple bond therein, said organic compounds in contact with water, comprising adding to said water in contact with said organic compounds an effective amount of a compound selected from the group consisting of erythorbic acid; an oxime of the formula:

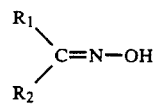

in which $R_1$ and $R_2$ are the same or different and are selected from hydrogen, lower alkyl groups of 1-8 carbon atoms and aryl groups; and mixtures thereof; wherein said water and said organic compounds are adjusted to a pH of about 7 to about 9.

2. The method of claim 1 wherein said compounds is added to said water in a process stream.

3. The method of claim 1 wherein said compound is erythorbic acid.

4. The method of claim 3 wherein said water and said erythorbic acid are adjusted to a pH of about 7 to about 9.

5. The method of claim 1 wherein said compound is an oxime.

6. The method of claim 1 wherein said compound is methyl ethyl ketoxime.

7. The method of claim 1 wherein said compound is added to said water at a level in the range of about 0.1 to about 100 parts per million parts of said water, by weight.

8. The method of claim 6 wherein the pH of said water is about 7 to about 9.

9. The method of claim 7 wherein said compound is methyl ethyl ketoxime.

10. A method of inhibiting fouling of organic compounds with at least one multiple bond therein in a process stream containing water, said process stream adjusted to a pH of about 7 to about 9, comprising producing an anti-foulant from an oxime of the formula:

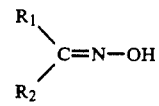

in which $R_1$ and $R_2$ are the same or different and are selected from hydrogen, lower alkyl groups of 1-8 carbon atoms and aryl groups, by heating said oxime to at least about 85° C. in the presence of water at a pH of about 7 to about 9 and contacting said process stream comprising both said organic compounds and said water with said anti-foulant.

11. The process of claim 10 wherein said anti-foulant is produced while in contact with said process stream.

12. The process of claim 10 wherein said oxime is methyl ethyl ketoxime.

* * * * *